(«12») United States Patent
Oldenhof et al.

(10) Patent No.: US 6,407,314 B1
(45) Date of Patent: Jun. 18, 2002

(54) MICROSPORE-SPECIFIC PROMOTER FROM TOBACCO

(75) Inventors: Margryt Teatske Oldenhof, Wageningen; George Joseph Wullems, Molenhoek; Jan Antonius Maria Schrauwen, Nijmegen; Michiel Maurits Van Lookeren Campagne, Wageningen; Johannes Bernardus Maria Custers, Wageningen; Johannes Jacobus Maria Dons, Wageningen, all of (NL)

(73) Assignee: Plant Research International B.V. (NL)

( * ) Notice: Subject to any disclaimer, the term of this patent is extended or adjusted under 35 U.S.C. 154(b) by 0 days.

(21) Appl. No.: 09/117,609
(22) PCT Filed: Feb. 14, 1997
(86) PCT No.: PCT/NL97/00066
§ 371 (c)(1),
(2), (4) Date: Jan. 22, 1999
(87) PCT Pub. No.: WO97/30166
PCT Pub. Date: Aug. 21, 1997

(30) Foreign Application Priority Data

Feb. 16, 1996 (EP) .............................. 96200318

(51) Int. Cl.[7] .......................... C12N 15/29; C12N 5/04; C12N 15/82; A01H 5/00; A01H 5/10
(52) U.S. Cl. .................... 800/287; 435/320.1; 435/419; 435/468; 536/24.1; 800/298
(58) Field of Search .............................. 435/69.1, 320.1, 435/410, 419, 468; 536/23.6, 24.1; 800/278, 287, 290, 295, 298

(56) References Cited

FOREIGN PATENT DOCUMENTS

| EP | 0344029 | 11/1989 | ............ C12N/5/00 |
| EP | 0436467 | 7/1991 | ............ C12N/15/29 |
| WO | 9008828 | 8/1990 | ............ C12N/15/82 |
| WO | 9325695 | 12/1993 | ............ C12N/15/82 |
| WO | 9401572 | 1/1994 | ............ C12N/15/82 |
| WO | 9421804 | 9/1994 | ............ C12N/15/82 |

OTHER PUBLICATIONS

Weterings, Koen, et al. "Functional dissection of the promoter of the pollen–specific gene NTP303 reveals a novel pollen–specific, and conserved cis–regulatory element." The Plant Journal, 8(1) (1995) pp. 55–63 XP002033052.

Albani, Diego, et al. "A Brassica napus gene family which shows sequences similarity to ascorbate oxidase is expressed in developing pollen. Molecular characterization and analysis of promoter activity in transgenic tobacco plants." The Plant Journal, vol. 2 (1992) pp. 331–342 XP002033053.

Thorsness, Mary K., et al. "A Brassica S–Locus Gene Promoter Targets Toxic Gene Expression and Cell Death to the Pistil and Pollen of Transgenic Nicotiana." Developmental Biology. vol. 143 (1991) pp. 173–184 XP000676323.

Oldenhof, M. T., et al. "Isolation and characterization of a microspore–specific gene from tobacco." Plant Molecular Biology, vol. 31 (1996) pp. 213–225 XP002032928.

Schrauwen, J.A.M., et al. "Stage–related expression of mRNAs during pollen development in lily and tobacco." Planta, 182 (1990) pp. 298–304 XP000576207.

Albani, Diego, et al. "Characterization of a pollen–specific gene family from Brassica napus which is activated during early microspore development," Plant Molecular Biology, vol. 15 (1990) pp 605–622 XP002007738.

Primary Examiner—Amy J. Nelson
Assistant Examiner—Ashwin Mehta
(74) Attorney, Agent, or Firm—Ladas & Parry

(57) ABSTRACT

The present invention is drawn to an isolated purified DNA sequence from the promoter region of a microspore-specific gene of tobacco. The microspore-specific promoter can play a role in the expression of genes in microspores. The invention also is drawn to chimeric genes suitable for transforming plants comprising the microspore-specific promoter. Further, the invention is also drawn to plants transformed with the chimeric genes.

7 Claims, 5 Drawing Sheets

```
       pollen      other
       development  plant tissues
       ─────────── ──────────────────
       Mi EBi MBi LBi  Pi  FB  Se  L  R  St
```

650 bp—

```
BamHI
GATCCAGATTTATAGGGTCCTAATGCGGGTACTGAACACCAGGTGGGAAACAAAAAATAT  -893
ACAGAACAACTCCTTTAGAATTTACAATTTTTGAGCGTGTTGGCTTGGTACGATTCTACT  -833
TTTCATATCTCTCGTCATCTCCTAACTCCTATGGTTCACCAGCCACCGATTAATTATGAC  -773
ACCGCTAACAAAAATCTTGCGACGACATTGAGAGAAATTTCTTTTCATAAATTGGTAATT  -713
CGTACATCATTTATAGGCGTTAGCTATAACCTTTTAGTTAGTGAATACAATACTTTTGC   -653
TATTATTATGTAACTTTTAGATATGAATTTACTTTCAAAAAAAAAAAAGGATCGATGTT   -593
GGTTATCAACTAAGGACCAACCACTTTGGACGTCTCACCACTAAGTTAAATAAATCACTT  -533
TGTTCTCGAAAAAAACCCCAAAAGTGTTAAAATGCTTTTCATATCATAATCAAACAACGT  -473
GATTAATAAAATCTATTAAGTTAATAGAAGTAGGGAATAAATCGGGCAAAGAATTTGAT   -413
ACAAACCAAACCGGTCAAAAAGCTAGTATTCATATAAATGGACTATACAAGTTAATACC   -353
AGCTAGCAGAAATTAAATAGTTTATTAAGTTGATTACAAAACAATTCCTCATTTAAAAAA  -293
AGTTAATGTAATCAAGAGATCTTTTGCTTCTAATTGATCAGACGAGGACCCCTCTTATTT  -233
ATTTTCTTTTTCATATAAGATTTTGAATAGATATAGGGAAATCTTGTTCACTCTTTATCT  -173
ACTTCAAATTGCATGCATTTTAAGAATTCTCTTTGTATGCAAACTTCAGTATTTATGATT  -113
GACATAAATCAATATTCATATCTTCGATAAAGTTAATAACTCTCCTAATACTTATGAATA  - 53
TCTCTTCCTTTACAACCCTATAAAACCCCCACTATAGCTACCTTCATAATTCATCTTAG  + 7
                      ____                            ▲
                    NcoI
AGTACCAACCCTAAATTTCTTAGTGATTAACCATGGCTAAGAAAAGTCTCACTTTTCTCA  + 67
                              M  A  K  K  S  L  T  F  L     aa 9

TTTGCATTTTCCTACTTCTCAATTTATGTTTTGCAATTGAGAACGTAGAAACTATGCAAA  +127
 I  C  I  F  L  L  L  N  L  C  F  A ⇔I  E  N  V  E  T  M  Q   aa29

AATCGGATTCATCGTCACAAGATAAAGAATTAGATTGGTTTCATCCGTGGTTCCATCCAC  +187
 K  S  D  S  S  Q  D  K  E  L  D  W  F  H  P  W  F  H  P      aa49
                                  _  _  _  _  _  _  _  _
                                               *  *
ATCCATGGTGGCTACATCCACATCCATGGCCATTCGTTCATCCGCCAATGCCAGCTGGCG  +247
 H  P  W  W  L  H  P  H  P  W  P  F  V  H  P  P  M  P  A  G   aa69
 *  *  *        *  *  *  *  *                 _____
GTTTTCATCATGCATGGCCATTCCCCCATCCACCGATGCCTGCTGGTGGTTTTAAGTTTC  +307
 G  F  H  H  A  W  P  F  P  H  P  P  M  P  A  G  G  F  K  F   aa89
 ____          (V)                    _____
CTCATCAATAATTTCATCGTCATCCATGGCCATTCATGCATCCACCAGTTCCATCTCCAC  +367
 P  H  Q                                                       aa92
CTAAAGGAGACAAGAATTAATTGAAAATATGAAGAGAAGTGTTGGATCAACATCTTATTG  +427
ATCACATATTTTTCTTTAGGTTAATATCTTTAGGATTTATGTCTTAGGTTATTTTGATA   +487
AAAATTAAAATAAATGATCGTTCTAGGGTAGTTATTATAATTTCTTAGATTTTTCCAAGT  +547
AGCTTTCGATGGTAGAAATGTTATTAATTTGATTCGGCTTATCATGAAATAAAATCCGTA  +607
GTATTATTGCTTTAGCTTTTATGATTTGTAGTTATTTATGTTGATTGTTCTCCATTT     +665
```

MICROSPORE-SPECIFIC PROMOTER FROM TOBACCO

FIELD OF THE INVENTION

The present invention is related to isolated, purified DNA sequences which can act as promoters in eukaryotic cells. More specifically, the present invention is related to such DNA sequences from tobacco which act as microspore-specific promoters and play a role in the expression of genes in microspores. This invention is also directed to chimeric genes suitable for transforming a plant comprising a structural gene under the control of the microspore-specific promoter. Further, this invention relates to plant cells and plants transformed with said chimeric gene.

BACKGROUND OF THE INVENTION

In angiosperm plants, sexual reproduction requires the production of viable male and female gametophytes. Pollen, as the male gametophyte, is formed within the anther and is initiated from sporogenous cells, which develop into meiocytes. The meiocyte undergoes meiosis to form a tetrad of haploid microspores which are subsequently released into the anther locule. Following expansion and vacuolation an asymmetrical mitosis of the microspore results in bicellular pollen, containing a vegative and generative cell. In the majority of plant species, including tobacco, pollen is shed in a bicellular condition. In other plant species (e.g. cereals and Brassica sp.), pollen maturation includes the mitotic division of the generative cell such that pollen is shed in a tricellular condition.

The morphological aspects of pollen development have been studied in great detail but knowledge about the underlying molecular processes is relatively limited. Pollen formation requires coordinated gene expression in the gametophytic cells and the sporophytic tissues surrounding it. Two periods of temporal gene expression are defined in pollen development by Mascarenhas [20]. The early developmental stage starts after meiosis and ends with the microspore mitosis, the lace stage covers the period after mitosis up to mature pollen [14]. During pollen development the mRNA content present in different stages changes qualitatively [28]. Genes which are transiently and specifically transcribed during pollen development are assumed to play a crucial role in the developmental processes. Summarizing, genes involved in pollen development can be classified, according to expression pattern as early [8, 29, 35], and late genes [3, 6, 21, 32, 39, 40]. Additionally, genes transcribed in both stages have been isolated [1, 25, 33].

This classification does not use the place of expression in consideration. If this localisation is taken as an extra criterion, the previous classification can be refined, which leads to four categories of pollen developmental genes. First, a category of genes with exclusive expression in the unicellular microspore; second, a group with localised expression in the diploid anther tissues during development; third, a group which localised expression in pollen; and fourth, a group with expression in unicellar microspores, pollen and diploid anther tissues. Genes of the first category have not been identified yet.

Previous studies of early genes restricted to microsporogenesis resulted in a group of genes of which expression [8, 29, 35] is localised in the tapetum or other anther tissues. A few genes have been characterised which are expressed in both developing pollen and in tapetum [25, 30, 33].

It is an object of the present invention to isolate and characterize a DNA sequence which is capable of acting as a microspore-specific promoter. More particularly, it is an object of the invention to isolate and characterize a microspore-specific promoter region taken from a microspore-specific gene.

SUMMARY OF THE INVENTION

The present invention relates to an isolated, purified DNA sequence, SEQ ID NO:1 from the promoter region of a microspore-specific gene of *Nicotiana tabacum*, upstream of a sequence encoding a protein comprising the amino acid SEQ ID NO:2 sequence set forth in FIG. 2 or a protein substantially homologous therewith.

The present invention further relates to an isolated purified DNA sequence from the promoter region of a microspore-specific gene of tobacco, the sequence consisting essentially of nucleotides −952 to +43 set forth in FIG. 2 or a functional fragment thereof having promoter activity.

Further this invention provides chimeric genes suitable for transforming a plant, comprising a DNA sequence as defined above and a naturally occurring or synthetic gene which is under the control of said DNA sequence.

The promoter of this invention is shown to be exclusively active in the male reproductive cell of a higher plant during early pollen development. Transcripts were observed only in the unicellular microspore. There is no expression in the sporophytic tissues that represent the majority of cells in the anther, nor in any other tissue of the plant. Expression is also developmently restricted to the unicellular microspore: the promoter is inactive during the preceding tetrad stage and the activity disappears at microspore mitosis.

Some authors reported microspore-specific genes like Bp4 [1 and PCT application WO 90/08828] and Bp19 [2] in *Brassica napus*. But the term microspore was also used for the bicellular pollen. In contrast our definition for microspore is for the unicellular stage of pollen development.

In the present Examples the BamHI-NcoI fragment consisting of nucleotides −952 to +43 set forth in FIG. 2 was used as promoter. The functionality of the promoter was established in a transgenic context. For this purpose the promoter was placed before the gus-reporter gene. Further it was established that the promoter is not at all active in tissues other than microspores. For this purpose the promoter was placed before the barnase gene. The ATG of the NcoI site was used as translational start. The promoter-gus and promoter-barnase cassettes were transferred in a binary plasmid and introduced in tobacco by *Agrobacterium tumefaciens* transformation.

As a comparison similar constructs were made with Bp4 promoter described in [1] and in WO 90/08828. The Bp4 promoter was cloned from *Brassica napus* using PCR amplification. Said promoter contained nucleotides 7 to 265 of FIG. 3a in WO 90/08828 and flanking HinDIII and XbaI restriction sites. Said promoter is the Bp4A promoter. FIG. 7c of WO 90/08828 discloses a 490 bp chimeric promoter of Bp4C and Bp4A. Since the Bp4A and Bp4C promoters are substantially identical, the promoter disclosed in WO 90/08828 will be functionally identical with the Bp4 promoter used in the present Examples.

The results of the comparison tests show that the present promoter is a strong and evidently microspore-specific promoter. The Bp4 promoter, however, is a second phase promoter which is only active after the first pollen mitosis. Further, the Bp4 promoter is a wean promoter as compared with the present promoter.

The present promoter importantly offers the opportunity to manipulate unicellular microspore-specific expression of genes introduced in the plant by genetic engineering. These sequences can be used to limit the expression of any given DNA-sequence to microspores and to microsporogenesis up to microspore mitosis. The microspore-specific promoter can be used to limit the expression of DNA sequences adjacent to it, to microspores in the Solanacae family and it is fully believed that these DNA sequences or functional fragments thereof will function as microspore-specific promoters in numerous other if not all microspore-bearing plant species that are capable of being genetically transformed.

These microspore-specific promoters can be used in conjunction with naturally occurring or synthetic flanking sequences critical to microspore development.

It should be noted that the identification of a promoter region is usually defined by function rather than a set DNA sequence. The expression "a functional fragment thereof having promoter activity" as used herein means generally a fragment of the defined promoter region sequence consisting of sufficient nucleotides upstream from the 3' end of the promoter region to have promoter activity. As little as 80 to 200 bases may be sufficient DNA sequence to maintain the tissue-specificity and promoter function. It should also be recognized that some upstream DNA sequences can be arranged in opposite orientations and still retain or demonstrate enhanced promoter function. In addition, "enhancer-like" DNA sequences, which are usually small conserved DNA sequences ranging in size from less than 10 nucleotides to considerably larger numbers of nucleotides can also be inserted into promoter regions to enhance expression.

The chimeric gene of the invention can comprise any gene or gene fragment, whose expression product (RNA and/or protein or polypeptide) causes changes in metabolism, functioning and/or development of microspores. Such a gene may preferably be a male-sterility gene. Since the promoter Us microspore-specific, other plant functions or tissues are not affected as is shown in the Examples. Preferred male-sterility DNAs are described in EP-A-89401194.9, for example those DNAs encoding: RNases such as RNase T1 or barnase; DNases such as endonucleases (e.g., EcoRI); proteases such as papain; enzymes which catalyze the synthesis of phytohormones (e.g., isopentenyl transferase or the gene products of gene 1 and gene 2 of the T-DNA of Agrobacterium; glucanases; lipases; lipid peroxidases; plant cell wall inhibitors; or toxins (e.g., the A-fragment of diphteria toxin or botulin). Other preferred examples of male-sterility DNAs are antisense DNAs encoding RNAs complementary to genes, the products of which are essential for the normal development of fertile pollen. Further preferred examples of male-sterility DNAs encode ribozymes capable of cleaving specifically given target sequences of genes encoding products which are essential for the production of fertile pollen. Still other examples of male-sterility DNAs encode products which can render stamen cells, particularly microspores—and not other parts of the plant— susceptible to specific diseases (e.g. fungi or virus infection) or stress conditions (e.g. herbicides).

The present invention also relates to a plant cell or plant cell cultures transformed with the chimeric gene comprising the gene the wild-type promoter of which is replaced by the promoter DNA sequence of the invention. Further, the invention relates to a plant or its seeds consisting essentially of said plant cells.

BRIEF DESCRIPTION OF THE FIGURES

FIG. 2. Nucleotide and deduced amino acid sequence of the NTM19 gene (SEQ ID NO:1 and SEQ ID NO:2, respectively). The TATA box and polyadenylation site are underlined, the transcription start is marked with an arrowhead. The change in amino acid in the cDNA clone from cv. Petit Havana relative to the genomic clone from cv. Samsun is bracketed. A possible cleavage site for the signal sequence is indicated by a double arrow. Three repeats in the amino acid with a length of 9, 5 and 4 residues are shown by resp. dashed lines, asterisks and continuous lines. A possible phosphorylated serine is double underlined.

DETAILED DESCRIPTION OF THE INVENTION

Materials and Methods

Plant Material

Figure 1:
FIG. 1. Northern blot analysis of the expression of gene NTM 19. Twenty-five µg total RNA from pollen at different developmental stages and different plant tissues was hybridised with a $^{32}$P-labelled NTM19 cDNA probe. Abbreviations: Mic=microspores, EBi=early binucleate pollen, MBi= mid binucleate pollen, LBi=late binucleate pollen, Pi=pistil, FB=flower buds without anthers, Se=seedling, L=leaf, R=root tips, St=stem. The size of the mRNA was determined with the ribosomal bands as markers.

Plants of *Nicotiana tabacum* L. cv. 'Petit Havana' SR1 [19], were grown in soil under greenhouse conditions. Flower buds of selected length were collected to obtain pollen of different developmental stages. The determination of developmental stage and isolation of the anther content was carried out as previously described [28].

Nucleic Acid Isolation

RNA was isolated with guanidine thiocyanate as RNase inhibitor by the procedure of Cathala [4] with minor modifications. All plant tissues including the microspores were frozen in liquid nitrogen and ground in a prechilled mortar.

The ground material was placed in 2 ml lysis buffer and, after centrifugation at 3000 g for 10 min at 15° C., the supernatant was collected. The duration of all centrifugation steps in the procedure was modified from the original procedure to 20 min.

The mRNA to be used for the synthesis of the cDNA library was bound on the surface of oligo(dT) Dynabeads (Dynal) as described by the manufacturer [10]. The mRNA used to synthesize a single-stranded cDNA probe was isolated as reported [26]. Plasmid DNA was isolated according to standard procedures [26], genomic DNA as reported [5] and phage DNA was obtained with LambdaSorb Phage Adsorbent according to the manufacturer's protocol (Promega).

cDNA Library Construction and Screening

A cDNA library in λ ZAP II [31] was made from mRNA isolated from microspores. The cloning kit and the Gold Packaging Extract of Stratagene were used according to the manufacturer's protocols. The cDNA library was amplified once prior to screening.

Differential screening was carried out with $^{32}$P labelled single-stranded cDNA probes derived from either mRNA from microspores or young leaves. The screening procedure of Stratagene was followed at a hybridisation and washing temperature of 55° C. The filters were washed in steps of 30 min in SSC with 0.1% (w/v) SDS (1×SSC=150 mM NaCl, 15 mM Na citrate, pH 7). The SSC concentration was lowered in steps; 6×SSC, twice in 2×SSC followed by 0.5×SSC and 0.2×SSC. A primary library screening of 2×10⁻ cDNA clones was done.

The single-stranded cDNA probes were made as described [251] with the following changes: 2 µg mRNA, oligo(dT), 75 µCi [α-$^{32}$P]dATP (3000 Ci mmol$^{-1}$) and 400 units 'Superscript' reverse transcriptase from BRL were used to prime and radiolabel the probe. Selected plaques were isolated and excised in vivo from the λ ZAP II phagemid to form a pBluescript SK-plasmid according to the procedure of Stratagene.

Genomic Library Screening

The genomic library of *Nicotiana tabacum* cv. Samsun in bacteriophage λ Charon 32 [12] was a generous gift of Dr. R. B. Goldberg [15], *E.coli* K802 cells were used as hosts. A cDNA of 240 bp comprising part of the 3' end region was used to synthesize a random-primed probe labelled with [α-$^{32}$P]dATP as described previously [7]. The screening and hybridisation were carried out using standard techniques [26]. Hybridisation and washings were done at 65° C., with stringent washing up to 0.1×SSC, 0.1% SDS. A positive clone of 11 kbp was digested with KpnI and XhoI. A digested fragment of 3 kbp containing the sequence of interest was subcloned into the plasmid pGEM 7Zf+ (Promega) using standard methods [26].

Northern and Southern Analysis

Samples of 25 µg of total RNA were denatured, electrophoresed on a 1% (w/v) agarose formaldehyde gel, and capillary-blotted on Hybond-N membrane (Amersham) as reported [26]. The rRNA bands were used as size markers. The RNA was bound to the membrane by baking for 2 hours at 80° C. The same probe was used as for the screening of the genomic library. Hybridisation was carried out overnight at 65 ° C. in 6×SSC, 5×Denhardt's reagent, 0.5% SDS and 100 µg/ml denatured herring sperm DNA. Washing was done at the sane temperature during 30 min in 6×SSC, 0.1% SDS followed by 2×SSC, 0.1% SDS. An actin probe was hybridised to the stripped northern blot as a control.

Southern analysis of 10 µg genomic DNA was done after restriction digestion and electrophoresis on a 0.8% agarose gel using standard methods [261] except the depurination, which was carried out by UV-irradiation. Southern blots were hybridised overnight at 60° C., and washed to a stringency of 0.4×SSC at 60 ° C. The probe used in Southern analysis was made of a fragment of 250 bp including partial 5'noncoding and 5'coding regions. Filters were exposed to Kodak X-OMAT AR film with intensifying screens at −80° C.

Sequence Analysis

DNA sequencing was performed by the dideoxy chain termination method [27] with the use of T7 polymerase (Pharmacia). The genomic clone was subcloned in pGEM 7Zf+ (Promega). Sequencing was performed with part single-stranded and double-stranded template DNA [41]. Sequence data were analysed with the PC/Gene programme from Intelligenetics Inc. Geneva (Switzerland).

In Situ Hybridisation

Anthers were collected for in situ hybridisation from tobacco flower buds of varying lengths (6, 8, 12, 20, 30 and 48 mm) covering a broad range of pollen developmental stages, from pollen mother cells to mature pollen. By use of a light microscope, the selected pollen developmental stages are distinguished clearly by their morphological characteristics visible after a DAPI-staining [28].

The procedure as described by Reijnen et al. [241] was used with the following modifications. Prior to fixation the too of the anther was cut to optimise penetration of the fixative. Fixation was done for 12 hours and initiad with degassing for 15 min. Washing after hybridisation was started with 2×SSC for 15 min at room temperature and coverslips removed. Subsequently, an RNase A treatment 20 µg ml$^{-1}$ in 0.5 M NaCl, 10 mM Tris-HCl (pH 7.5), 1 mM Na$_2$ED-TA) was carried out for 45 min at 37° C. The slides were washed twice in 2×SSC, 1 mM DTT (dithiotreitol) for 30 min at 37° C., followed by 0.2×SSC, 1 mM DTT for 1 hour at 45° C.

The NTM19 RNA probes were synthesised by in vitro transcription in sense and antisense orientation from a cDNA subclone in pBluescript, that contained a 200 nt part of the coding region. The sense probe was used as a negative control. The protocol of Promega was followed with the use of [5,6-$^3$H] UTP and for each slide 2×10$^5$ c.p.m. were used in hybridisation. After processing of the slides, anthers were stained in 1 µg ml$^{-1}$ ethidium bromide for 5 min and washed in distilled water for 20 sec. A confocal laser scanning microscope (BioRad MRC-500) was used to analyse the sections. Pictures were made combining those made from a fluorescent image resulting from ethidium bromide staining, with a reflection image that visualized silver grains which are formed if the probe used hybridises to the section.

Determination of the Transcription Initiation Point

To determine the transcription start site, the primer extension technique was used as previously described [341]. A 30-mer primer was chosen 30 nt downstream of the translation start point, with the help of a primer programme (Biosciences Inc. Plymouth, USA) and the PC Gene programme (Intelligenetics Inc., Geneva, Switzerland). The latter programme was used to localise secondary structures in the RNA. The longest possible secondary structure was prevented from forming by blocking this region using hybridisation of the 30-mer primer.

EXAMPLES

Example 1

Isolation of cDNA and Genomic Clone; Characteristics of the Transcript

Microspores of tobacco at an early stage were isolated as described in Materials and Methods. Poly A$^+$ RNA was prepared from these cells and used to synthesise a cDNA library. The primary library contained 1.6×10⁶ recombinants and was amplified once. Differential screening was done with cDNA from leaves as a negative probe. From the selected microspore-positive and leaf-negative clones, 10 clones were tested for tissue—and pollen developmental stage-specific expression by Northern analysis. This analysis resulted in 2 microspore-specific cDNA clones; one of these clones called "NTM19" (*Nicotiana tabacum* microspore-specific) was characterized.

FIG. 1 shows the results of a northern blot containing total RNA prepared from isolated microspores and pollen at different stages of development: hybridised with NTM19. Other plant tissues, namely: pistil, flower bud of which anthers were removed, seedling, leaf, root tips and stem were also included in this analysis. No hybridisation signal was observed in the lanes with RNA from the bicellular pollen stages or any other plant tissue. The position of the signal corresponded to a transcript length of about 650 nt. The NTM19 cDNA clone has a length of about 500 bp, and is therefore not a full length clone.

To complete the sequencing of the transcript a corresponding genomic clone was isolated. The available and presumed 3' non-coding region of cDNA clone NTM19 was used as a probe to screen a genomic tobacco library in λ Charon 32. In the non-coding parts of the transcript the restraint on evolutionary divergence is low and therefore this sequence accurately identifies the corresponding gene. The use of a non-coding region as a probe diminishes the chance of isolating a related gene from a gene family. The genomic clone corresponding to the NTM19 cDNA clone was successfully isolated using this procedure.

After the isolation of hybridising genomic clones, the entire cDNA was used to probe restriction fragments of the selected clones. A subclone was made that covered the region of a genomic clone hybridising to the cDNA clone. Another subclone overlapping the former one and protruding in the 5' direction was also constructed.

Example 2
Sequence Characterisation and Start of Transcription of the NTM Gene

To identify the NTM19 gene, a sequence analysis of the two genomic subclones and the cDNA clone was performed (FIG. 2). The longest open reading frame covering the cDNA region was selected. From the cDNA region and from the corresponding genomic clone an open reading frame was deduced ranging from position +40 to +316 bp, relative to the transcription start, encoding a protein of 92 amino acids. The translation initiation region, 6 nucleotides immediately upstream and 3 nucleotides downstream of the ATG start codon, conforms well to the consensus in other plant genes [16] and thus supported the choice of reading frame. The putative polyadenylation signal [12] is underlined in FIG. 2 and is at a distance of 20 nucleotides followed by a poly (A)tail of 18 nucleotides in the cDNA clone.

Figure 3:
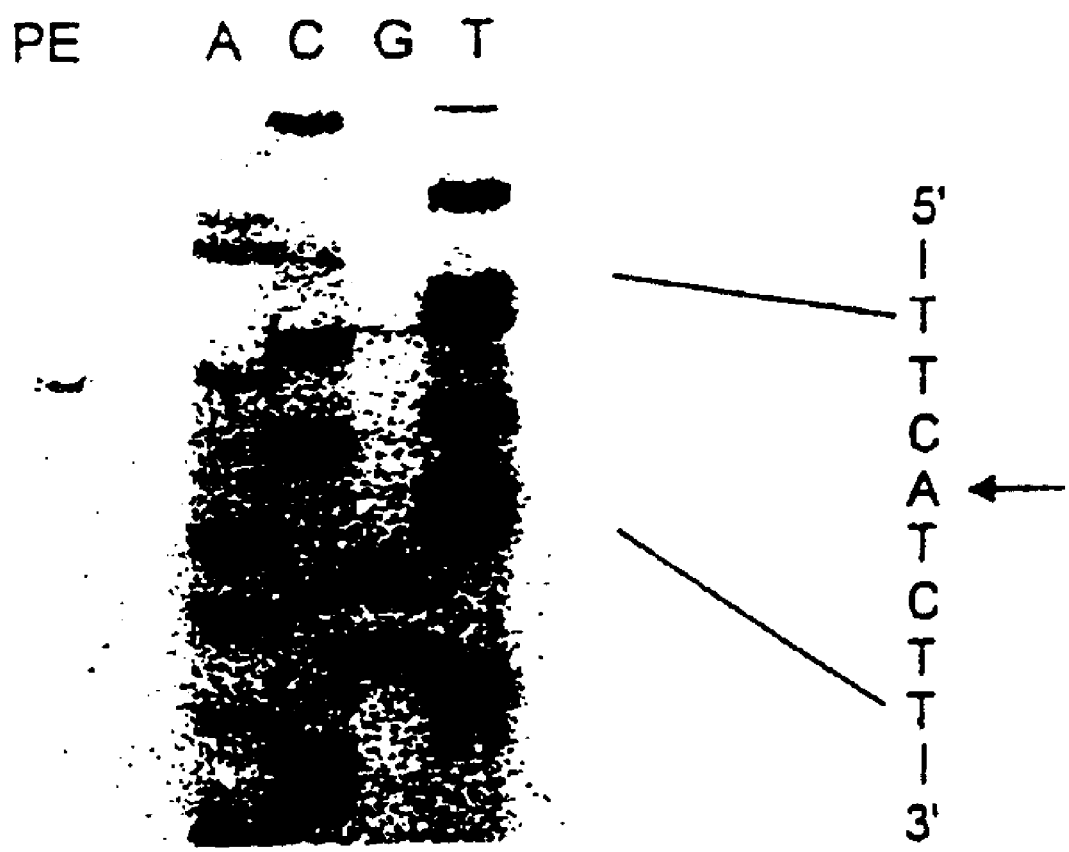
FIG. 3. Identification of the transcription start of the NWM19 gene. Primer extension analysis (PE) and plasmid sequencing (ACGT) were performed using the same NTM19-specific synthetic oligo-nucleotide with sequence 5'-TGCAAAACATAAATTGAGAAGTAGGAAAAT-3' (SEQ ID NO:3 complementary to the nucleotides between positions (+)66 and (+)103 and $^{32}$P labelled). The nucleotide sequence at the 5' end is reported. The arrow indicates the position of the primer extension product.

The transcription start was determined by primer extension analysis (FIG. 3). The first transcribed nucleotide is an adenine (A) at a distance of 39 nt from the start codon, marked in FIG. 2 by an arrowhead and denoted as position +1. This is in accordance with the fact that in plant genes, adenine is the most common nucleotide at the transcription start site [13]. The putative TATA box is 35 nt upstream from the transcription start and underlined in FIG. 2. The distances between TATA box, transcription start and first AUG codon fit well within the range determined for a large number of plant genes [13].

The coding region of the genomic clone is almost identical to that present in the cDNA. Two nucleotide differences are noted at nucleotide positions +74 and +132, and no intervening sequences were seen. The transcribed region of the genomic clone has a length of 658 bp, including the 18 nt poly(A) tail that starts at sequence position +641. This is in good agreement to the estimated transcript length of 650 nt determined from the Northern blot. Therefore it is inferred that no introns are present in the NTM19 gene.

Database searches did not reveal any significant homology to nucleotide sequences (Genbank, EMBL) or polypeptide sequences (SwissProt, PIR). Therefore the NTM19 gene represents a novel sequence.

Example 3
Characteristics of the NTM19 Protein

The properties of the NTM19 protein were deduced from computer analysis. In FIG. 2 the deduced amino acid sequence of the NTM19 gene is given.

The two differences in nucleotide sequence between the genomic and cDNA clone result in a change of one amino acid. One C in the genomic clone is replaced by a T in the cDNA clone, resulting in a change from alanine in the genomic sequence (bracketed at amino acid 74) to valine in the cDNA sequence. Because both amino acids have a similar chemical character, this substitution would not greatly change the properties of the protein. The second difference is at nucleotide position 132, a G in the genomic clone is replaced by a T in the cDNA clone without affecting the encoded serine residue (amino acid position 31). The sequence differences between genomic and cDNA clone were repeatedly found in independent sequencing experiments. The cDNA library was made from the cultivar Petit Havanna and the genomic clone from the cultivar Samsun. This may be the explanation for the sequence differences. The function of the NTM19 protein is unknown.

Example 4
Spatial and Temporal Expression Patterns of NTM19 in Anthers

Figure 4:
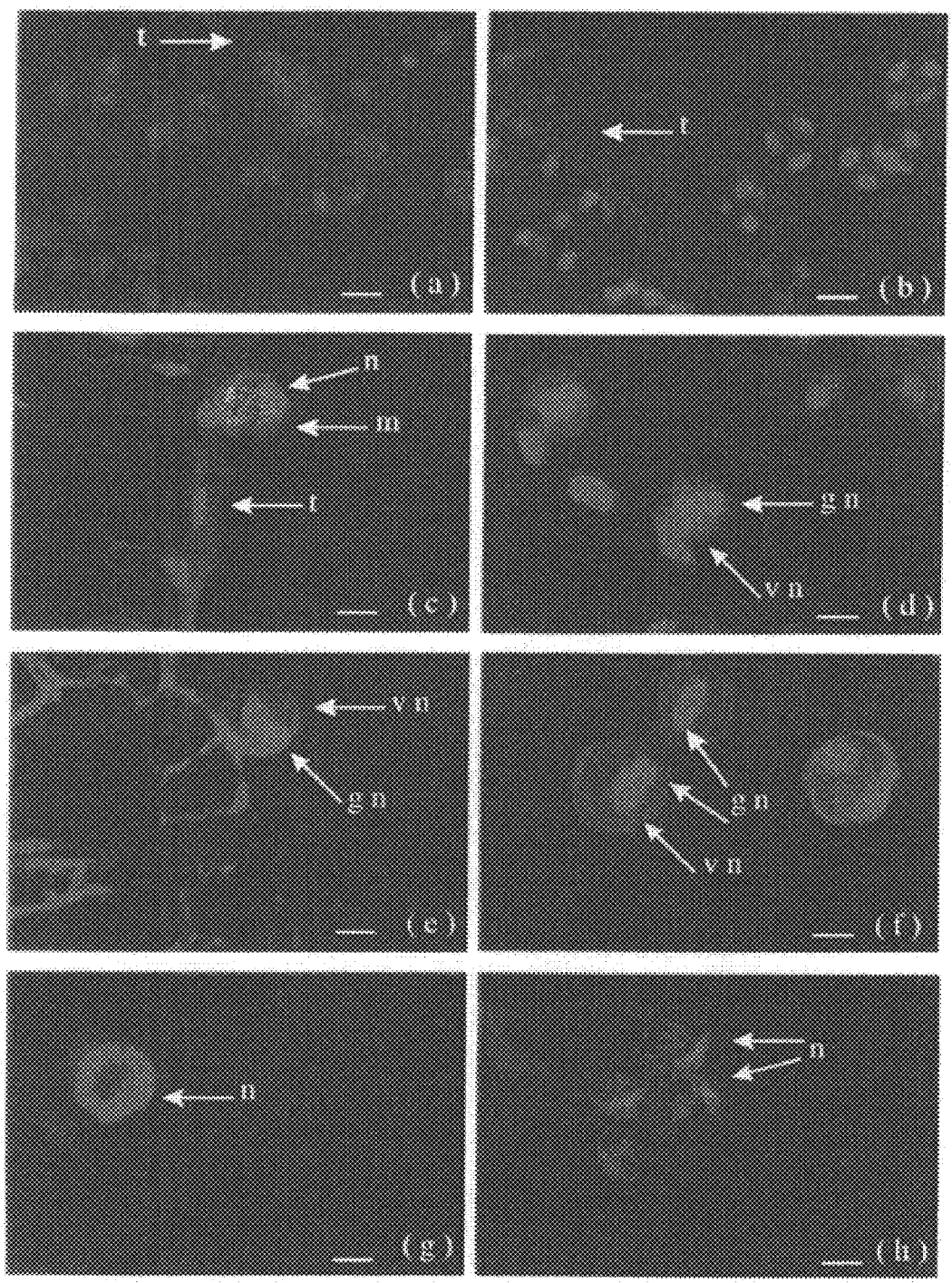
FIGS. 4a–h. Localisation of NTM19 mRNA during anther development in longitudinal sections of anthers by in situ hybridisation. a–g: combinations of fluorescence and reflection CLSM images of anther sections during the microspore stage and preceeding and successive pollen developmental stages, determined as described in Materials and Methods. Abbreviations: n=nucleus, vn=vegetative nucleus, gn=generative nucleus. Expression of NTM19 analysed in another sections with the antisense NTM19 probe: (a) pollen mother cells undergoing meiosis. (b) tetrads. (c) and (h) microspores; m=microspore with green spots which represent regions of RNA/RNA hybridisation, t=tapetum. (d) early bicellular pollen. (e) mid-bicellular pollen. (f) late bicellular pollen. (g) control section with microspore with the sense NTM19 of microspore. Bar=10, µm. In the bicellular pollen 2 nuclei are visible by a more intensive red staining, the mature pollen shows a characteristic discus shaped generative nucleus.

The precise temporal and spatial expression patterns of NTM19 were revealed by in situ hybridisation. This technique allows the accurate discrimination between sporophytic and gametophytic localisation of expression. FIG. 4 shows the localisation of NTM19 mRNA in longitudinal sections of tobacco anthers at different developmental stages. The antisense NTM19 RNA probe hybridised specifically with the microspore RNA and not with tapetum RNA. A hybridisation signal was not found in anthers with pollen mother cells undergoing meiosis, nor in tetrads, nor in bicellular pollen. The NTM19 sense RNA probe used as a negative control in all experiments gave no hybridisation signal.

Example 5
Construction of pNTM19-GUS

The genomic clone of NTM19 was digested with BamHI and HincII, and subcloned into BamHI and HincII cut pGEM-3Zf (+) (Promega corporation). The resulting plasmid was digested with KpnI and NcoI to release the NTM19 promoter. This fragment was used to replace the KpnI/NcoI LAT52 promoter fragment from plasmid pLAT52-7 [36] to give plasmid pMO4. pMO4 was digested with KpnI and SacI to release the, NTM19-GUS fusion, which was used for ligation into XpnI/SacI cut pEMBL19(−) (Boehringer Mannheim). The resulting plasmid pEMBL-NTM19GUS was digested with HindIII and SacI to release the NTM19-GUS fusion. This fragment was used to replace the HindIII/SacI 35S-CaMV promoter-GUS fragment of the binary plasmid pBI121 [11] to give the binary plasmid pNTM19-

GUS. pNTM19-GUS was transferred from *Escherichia coli* to the agropine *Agrobacterium tumefaciens* strain Ag10 [17] for use in plant transformation experiments.

Example 6
Construction of pBp4-GUS

Two oligo nucleotide primers were designed to fit the 5'-untranslated region of the Bp4A gene, spanning nucleotides 4–265 [1], and containing overhanging SalI and HindIII restriction sites at the 5'-end, and XbaI and BamHI restriction sites at the 3'-end. The sequences of these primers are as follows. Primer 1: 5'-GTC GAC AAG CTT CTA AAA ATA GCA ATA ACT-3', SEQ ID NO:4 and primer 2: 5'-GGA TCC TCT AGA AAG AGA TGA AGT ATT CTA-3', SEQ ID NO:5. After PCR amplification of the Bp4A promoter fragment from genomic DNA isolated from Brassica napus cv 'Topas', the resulting 282 bp DNA fragment was digested with HindIII and XbaI, and cloned into HindIII/XbaI cut pEMBL19(−) (Boehringer Mannheim). The resulting plasmid, pEMBL-Bp4, was used as Bp4 promoter source for all further experiments. The sequence of the isolated promoter was determined and compared to the published sequence derived from cv 'Westar' [1]. Two differences were detected: 1) a cytosine residue at position 203 was replaced by a guanine, and 2) a guanine at position 122 was replaced by cytosine [1]. The Bp4 promoter was exsised from pEMBL-Bp4 with HindIII and XbaI. This fragment was used to replace the HindIII/XbaI 35S-CaMV promoter fragment of the binary plasmid pBI121 [11] to give the binary plasmid pBp4-GUS. pBp4-GUS was transferred from *Escherichia coli* to the agropine *Agrobacterium tumefaciens* strain Ag10 for use in plait transformation experiments.

Example 7
Construction of pNTM19-barnase

A XbaI/EcoRV fragment from plasmid pWP126, containing an engineered barnase-barstar operon from Bacillus amyloliquefaciens and the CaMV polyadenylation sequence identical to pWP127 [23] was inserted into XbaI/SmaI cut pUCAP to give plasmid pR-barnase [38]. The SalI/NcoI NTM19 promoter fragment from pEMBL-NTM19GUS was ligated into SalI/NcoI cut pR-barnase to yield pUC-NTM19barnase. The entire NTM19 promoter-barnase-CaMV polyadenylation sequence cassette was excised from pUC-NTM19barnase with AscI and PacI, and transferred to AscI/PacI cut pBINPLUS [38]. The resulting binary plasmid, pNTM19-barnase was used for plant transformation after transfer to the agropine *Agrobacterium tumefaciens* strain Ag10 for use in plant transformation experiments.

Example 8

Construction of pBp4-barnase

The Bp4 promoter from pEMBL-Bp4 was excised with HindIII/XbaI, and transferred to HindIII/XbaI cut pUCAP. The AscI/XbaI Bp4-promoter fragment from this plasmid was transfered to AscI/XbaI cut pR-barnase, to give pUC-Bp4barnase. The entire Bp4 promoter-barnase-CaMV polyadenylation sequence cassette was excised from pUC-Bp4barnase with AscI and PacI, and transferred to AscI/PacI cut pBINPLUS [38]. The resulting binary plasmid, pBp4-barnase was used for plant transformation after transfer to the agropine *Agrobacterium tumefaciens* strain Ag10 for use in plant transformation experiments.

Example 9
Establishment of Transgenic Plants

For allowing functional analysis, the promoter constructs were introduced into tobacco (*Nicotiana tabacum* cv Petit Havana SR1), using the leaf-disc transformation method reported by [9]. Inocula of *Agrobacterium tumefaciens* Ag10 with the various promoter constructs were prepared by overnight culture, until OD 1 (550 mn), in liquid LB medium supplemented with 50 mg/l rifampicin +50 mg/l kanamycin. Leaf discs were punched from in vitro grown stock plants and immersed in inoculum diluted to OD 0.1 for 5 minutes, and then were blotted dry on filter paper. They were co-cultivated upside-down on agar-solidified MS-20 plates supplemented with 1 mg/l BA and without antibiotics for two days. Thereafter, the discs were transferred to the same medium supplemented with 250 mg/l cefotaxime, 200 mg/l vancomycin and 100 mg/l kanamycin. After 4 to 8 weeks, shootlets that developed from the leaf-disc edges were transplanted to MS-20 plates with the same antibioticum cocktail but without phytohormones, to allow shoot elongation and root formation. Plants that rooted on the kanamycin medium were considered to be transgenic, and were transferred into a glasshouse and grown to flowering.

Example 10
Histochemical GUS Assay

Kanamycin-resistant plants were analysed for the distribution of β-glucuronidase activity (GUS) using the method described by [11] with modifications as reported by [37]. Different plant tissues, including roots, stems and leaves, and all different parts of the flower, taken from a number of independent transgenic plants were analyses. For qualitative assessment of GUS activity in the microspores and pollen of successives stages of development (from microspore release from the tetrad until mature pollen), these were collected by sectioning anthers in GUS-extraction buffer and filtering through a 50 μm nylon mesh sieve. To enable exact determination of the microspore or pollen developmental stages, counter-staining was carried out by adding DAPI to a final concentration of 1.25 μg/ml followed by incubation at 45° C. for 8–16 h.

Example 11
Enzymatic GUS Assay

Microspores or pollen were collected as described above in M1S medium [42], washed once, counted, and pelleted. The pellet was stored frozed (−80° C.) untill used for quantitative enzymatic analysis. GUS activity was determined as described previously, using methylumbelliferyl glucuronide (MUG) as a substrate [22].

Example 12
Results of Histochemical GUS Assay (X-Gluc)

The X-Gluc assay is not quantitative, but is used to be able to correlate the β-glucuronidase activity with the precise developmental stage by comparing the X-Gluc staining with a DNA staining used here for assessing the developmental stage.

The NTM19 promoter gave a very strong blue staining from mid-unicellular microspore stage up to mature pollen. When the pollen were germinated on BK-medium staining decreased rapidly and disappeared after 5 hours. Other tissues were not stained, except for the top cells or trichomes in some transgenic plants. The Bp4 promoter became only active in the mid-bicellular stage and continued to be active up to the mature pollen stage. When the pollen were germinated staining disappeared within 1 hour. The promoter provided a staining which was substantially constant in all stages in which the promoters were active. However, the intensity of the staining produced by NTM19 was much stronger than that produced by Bp4.

Example 13
Results of Enzymatic GUS Assay (MUG Assay)

Figure 5:
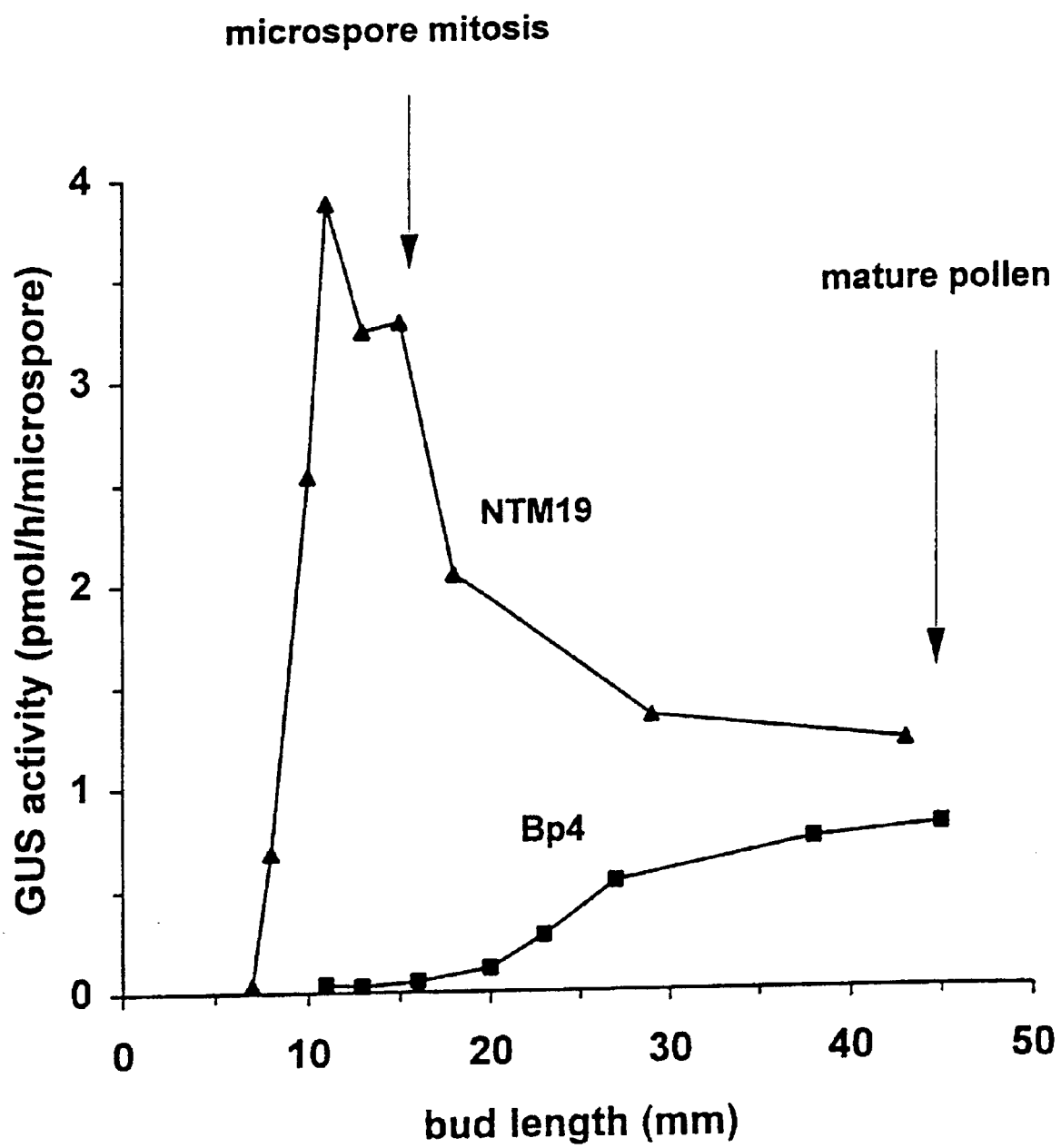
FIG. 5. Temporal pattern of GUS activity in microspores or pollen from transgenic tobacco plants transformed wish NTM19 promoter-GUS (triangles) or Bp4 promoter-GUS (squares) fusions. GUS activity is expressed as pmol 4-MU generated/hour/microspore or pollen. Microspore and poller developmental stages are correlated to the budlength.

MUG assay was carried out to determine quantitative differences in the amount of GUS protein. The activity of the NTM19 and Bp4 promoters started at the same stage as observed in the X-Gluc assays. The activity of NTM19 increased to a maximum at a bud length of about 16 mm (late unicellular up to first pollen mitosis) and subsequently decreased. The microspore mitosis occurs between 16 and 18 mm buds. The Bp4 promoter showed some activity from the 18 mm bud length stage, which was only significant from the 22 mm bud length stage. A maximum was reached which continued up to the mature pollen stage. The activity of the Bp4 promoter, however, was much lower than that of the NTM19 promoter. FIG. 5 shows the pattern of GUS activity.

Example 14
Analysis of Promoter-barnase Transgenic Tobacco Plants

When using the promoter-barnase constructs containing the NTM19 promoter or the Bp4 promoter, in both cases transgenic plants were formed. Consequently, the NTM19 and Bp4 promoters are not active during regeneration. When first callus was made on medium containing 2,4-D or NAA 1 mg/l+BA 0.25 mg/l and thereafter BA 1 mg/l, plants were formed too. Said assay was carried out starting from transgenic plant leaves. As regards the phenotype, when using the NTM19 promoter cells were killed in the mid-unicellular stage. Dead microspores are visible between mature pollen and during in vitro pollen germination. When using the Bp4 promoter cells were killed only after having reached the mid-bicellular stage.

On the basis of the percentages of killed microspores and pollen, respectively, plants having one locus and plants having more loci were found.

In all transgenic plants female fertility was maintained. All plants formed seed after self-pollination, but seed production decreased in plants having a high number of introduced copies. Said last mentioned plants did form the normal amount of seed after pollination with wild-type pollen.

No barnase activity was found in the various sexual reproduction stages. Further, in other tissues and organs of the transgenic plants, including the top cells of trichomes, no visible changes were found which would show barnase activity.

REFERENCES

1. Albani D, Robert L S, Donaldson P A, Altosaar I, Arnison P G, Fabijanski S F: Characterisation of a pollen-specific gene family from *Brassica napus* which is activated during early microspore development. Plant Mol Biol 15: 605–622 (1990).
2. Albani D, Altosaar I, Arnison P G, Fabijanski S F: A gene showing sequence similarity to pectin esterase is specifically expressed in developing pollen of *Brassica napus*. Sequences in its 5' flanking region are conserved in other pollen-specific promoters. Plant Mol Biol 16: 501–513 (1991).
3. Brander K A, Kuhlemeier C: A pollen-specific DEAD-box protein related to translation initiation factor eIF-4A from tobacco. Plant Mol Biol 27: 637–649 (1995).
4. Cathala G, Savouret J F, Mendez B, West B L, Karin M, Martial J A, Baxter J D: Laboratory methods. A method for isolation of intact, translationally active ribonucleic acid. DNA 2: 329–335 (1983).
5. Doyle J J, Doyle J L: Isolation of plant DNA from fresh tissue. Focus (Gibco/BRL) 12: 13–15 (1990).
6. Estruch J J, Kadwell S, Merlin E, Crossland L: Cloning and characterization of a maize pollen-specific calcium-dependent calmodulin-independent protein kinase. Proc Natl Acad Sci USA 91: 8837–8841 (1994).
7. Feinburg A P, Vogelstein B: A technique for radiolabelling DNA fragments to high specificity. Anal Biochem 137: 266–267 (1985).
8. Goldberg R B, Beals T P, Sanders P M: Anther development—basic principles and practical applications. Plant Cell 5: 1217–1229 (1993).
9. Horsch, R. B., Fry, J. E., Hoffmann, N. L., Wallroth, M., Eichholtz, D., Rogers, S. G., Fraley, R. T. (1985) A simple and general method or transferring genes into plants. Science 227, 1229–1231.
10. Jakobsen K S, Breivold E, Hornes E: Purification of mRNA directly from crude plant tissues in 15 minutes using magnetic oligo dT microspheres. Nucl Acids Res 18: 3669 (1990).
11. Jefferson, R. A., Kavanagh, T. A., Bevan, M. W. (1987) GUS fusions: β-glucuronidase as a sensitive and versalite gene fusion marker in higher plants. EMBO J. 6, 3901–3907.
12. Joshi C P: Putative polyadenylation signals in nuclear genes of higher plants: a compilation and analysis. Nucl Acids Res 23: 9627–9640 (1987).
13. Joshi C P: An inspection of the domain between putative TATA box and translation start site in 79 plant genes. Nucl Acids Res 15: 6643–6653 (1987).
14. Kenton A, Parokonny A S, Gleba Y Y, Bennett M D: Characterization of the Nicotiana tabacum L. genome by molecular cytogenetics. Mol Gen Genet 240: 159–169 (1995).
15. Koltunow A M, Truettner J, Cox K H, Wallroth M, Goldberg R B: Different temporal and spatial gene expression patterns occur during anther development. Plant Cell 2:1201–1224 (1990).
16. Kozak M: The scanning model for translation: an update. J Cell Biol 108:229–241 (1989).
17. Lazo, G. R., Stein, P. A., Ludwig, R. A. (1991) A DNA transformation-competent Arabidopsis genomic library in Agrobacterium. Bio/Technol. 9, 864–868.
18. Loenen W A M, Blattner R R: Lambda Charon vectors (Ch 32, 33, 34, 35) adapted for DNA cloning in recombinant-deficient hosts. Gene 26: 171–179 (1983).
19. Maliga P, Sz.-Breznowvitis A, Marton L: Streptomycin resistent plant from callus culture of haploid tobacco. Nature New Biol 244:29–30 (1973).
20. Mascarenhas J P: Gene activity during pollen development. Annu Rev Plant Physiol Mol Biol 41: 317–338 (1990).
21. Mu J-H, Lee H-S, Kao T-H: Characterization of a pollen-expressed receptor-like kinase gene of *Petunia inflata* and the activity of its encoded kinase. Plant Cell 6:709–721 (1994).
22. Nap, J. P., Dirkse, W. G., Louwerse, J., Onstenk, J., Visser, R., Loonen, A., Heidekamp, F., Stiekema, W. J. (1992) Analysis of the region in between two closely linked patatin genes: class II promoter activity in tuber, root and leaf. Plant Mol. Biol. 20, 683–694.
23. Paul, W., Hodge, R., Smartt, S., Draper, J., Scott, R. (1992) The isolation and characterization of the tapetum-specific Arabidopsis thaliana A9 gene. Plant Mol. Biol. 19, 611–622.

24. Reijnen W H, Vanherpen M M A, Degroot P F M, Olmedilla A, Schrauwen J A M, Weterings K A P, Wullems G J: Cellular localization of a pollen-specific messenger RNA by in situ hybridization and confocal laser scanning microscopy. Sex Plant Reprod 4: 254–257 (1991).
25. Roberts M R, Foster G D, Blundell R P, Robinson S W, Kumar A, Draper J, Scott R: Gametophytic and sporophytic expression of an anther-specific *Arabidopsis thaliana* gene. Plant J 3: 111–120 (1993).
26. Sambrook J, Fritsch E F, Maniatis T: Molecular cloning. A laboratory manual. Cold Spring Harbor Laboratory Press, Cold Spring Harbor, New York (1989).
27. Sanger F, Nicklen S, Coulsen A R: DNA sequencing with chain terminating inhibitors. Proc Natl Acad Sci 74: 5463–5467 (1977).
28. Schrauwen J A M, Degroot P F M, Vanherpen M M A, Vanderlee T, Reynen W H, Weterings I C A P, Wullems G J: Stage-related expression of messenger-RNAs during pollen development in lily and tobacco. Planta 182: 298–304 (1990).
29. Scott R, Dagless E, Hodge R, Paul or, Soufleri T, Draper J: Patterns of gene expression in developing anthers of *Brassica napus*. Plant Mol Biol 17: 195–207 (1991).
30. Shen J B, Hsu Fc: Brassica anther-specific genes: characterisation and in situ localization of expression. Mol Gen Genet 234: 379–389 (1992).
31. Short J M, Fernandez J M, Sorge J A, Huse W D: Lambda Z A P: a bacteriophage lambda expression vector with in vitro excision properties. Nucl Acids Res 16: 7583–7600 (1988). 32. Stinson J R, Eisenberg A J, Willing R P, Pe M P, Hanson D D, Mascarenhas J P: Genes expressed in the male gametophyte of flowering plants and their isolation.
Plant Physiol 83: 442–447 (1987).
33. Theerakulpisut P, Xu H L, Singh M B, Pettitt J M, Knox R B: Isolation and develop- mental expression of Bcp1, an anther-specific cDNA clone in *Brassica campestris*. Plant Cell 3: 1073–1084 (1991).
34. Triezenberg, S J: Primer Extension. Preparation and analysis of RNA. In Sharp P A (eds), Current protocols in Molecular Biology, unit 8.4.1. Greene Publishing Associates/Wiley Interscience, New York (1992).
35. Tsuchiya T, Toriyama K, Nasrallah M E, Ejiri S: Isolation of genes abundantly expressed in rice anthers at the microspore stage. Plant Mol Biol 20: 1189–1193 (1992).
36. Twell, D., Yamaguchi, J., McCormick, S. (1990) Pollen-specific gene expression in transgenic plants: coordinate regulation of two different tomato gene promoters during microsporogenesis. Development 109, 705–713.
37. van Altvorst, A. C., Riksen, T., Koehors:, H., Dons, H. J. M. (1995) Transgenic carnations obtained by *Agrobacterium tumefaciens*-mediated transformation of leaf explants. Trans. Res. 4, 105–113.
38. Van Engelen, F. A., Molthoff, J. W., Conner, A. J., Nap, J. P., Pereira, A., Stiekema, W. J. (1995) pBINPLUS: an improved plant transformation vector based on pBIN19. Transgenic Res. 4, 288–290.
39. Weterings K, Reijnen W, Vanaarssen R. Kortstee A, Spijkers J, Vanherpen M, Schrauwen J, Wullems G: Characterization of a pollen-specific cDNA clone from *Nicotiana tabacum* expressed during microgametogenesis and germination. Plant Mol Biol 18: 1101–1111 (1992).
40. Wing R A, Yamaguchi J, Larabell S K, Ursin V M, McCormick S: Molecular and genetic characterization of two pollen-expressed genes that have sequence similarity to pectate lyases of the plant pathogen Erwinia. Plant Mol Biol 14: 17–28 (1989).
41. Yie Y, Wei Z, Tien P: A simplified and reliable protocol for plasmid DNA sequencing: fast miniprep and denaturation. Nucl Acids Res 21: 361 (1992).
42. Zarsky, V., Garrido, D., Rihova, L., Tupy, J., Vicente, O., Heberle-Bors, E. (1992) Derepression of the cell cycle by starvation is involved in the induction of tobacco pollen embryogenesis. Sexual Plant Reproduction 5, 189–194.

What is claimed is:

1. An isolated and purified DNA sequence from the promoter region of a microspore-specific gene of *Nicotiana tabacum*, the DNA sequence consisting essentially of nucleotides 1–995 of SEQ ID NO:1.

2. A chimeric gene suitable for transforming a plant comprising a DNA sequence as defined in claim 1, and a naturally occurring or synthetic DNA coding sequence of interest which is under the control of said DNA sequence.

3. The chimeric gene according to claim 2, wherein the chimeric gene, when expressed microspores, causes changes in metabolism, functioning or development of microspores.

4. A plant cell or plant cell culture transformed with the chimeric gene of any of claim 2.

5. A plant regenerated from the plant cells of claim 4, wherein said plant comprises said chimeric gene.

6. The chimeric gene according to claim 2, wherein the chimeric gene when expressed in a microspore leads to male sterility.

7. A seed of the plant of claim 5, wherein said seed comprises said chimeric gene.

* * * * *

SEQUENCE LISTING

```
<160> NUMBER OF SEQ ID NOS:  5

<210> SEQ ID NO 1
<211> LENGTH: 1618
<212> TYPE: DNA
<213> ORGANISM: Nicotiana tabacum
<220> FEATURE:
<221> NAME/KEY: CDS
<222> LOCATION: (993)..(1271)
<221> NAME/KEY: sig_peptide
<222> LOCATION: (993)..(1056)
<221> NAME/KEY: mRNA
<222> LOCATION: (954)..(1574)
<221> NAME/KEY: polyA_site
<222> LOCATION: (1548)..(1594)
<221> NAME/KEY: TATA_signal
<222> LOCATION: (919)..(923)

<400> SEQUENCE: 1
gatccagatt tatagggtcc taatgcgggt actgaacacc aggtgggaaa c aaaaaatat     60 acagaacaac tcctttagaa tttacaattt ttgagcgtgt tggcttggta c gattctact    120 tttcatatct ctcgtcatct cctaactcct atggttcacc agccaccgat t aattatgac    180 accgctaaca aaaatcttgc gacgacattg agagaaattt cttttcataa a ttggtaatt    240 cgtacatcat ttataggcgt tagctataac cttttagtta gtgaatacaa t acttttgc     300
```

```
tattattatg taactttttag atatgaattt actttcaaaa aaaaaaaaag g atcgatgtt    360 ggttatcaac taaggaccaa ccactttgga cgtctcacca ctaagttaaa t aaatcactt    420 tgttctcgaa aaaaccccca aaagtgttaa aatgcttttc atatcataat c aaacaacgt    480 gattaataaa atctattaag ttaatagaag tagggaataa atcgggcaaa a gaatttgat    540 acaaaccaaa ccggtcaaaa aagctagtat tcatataaat ggactataca a gttaatacc    600 agctagcaga aattaaatag tttattaagt tgattacaaa acaattcctc a tttaaaaaa    660 agttaatgta atcaagagat cttttgcttc taattgatca gacgaggacc c ctcttattt    720 attttctttt tcatataaga ttttgaatag atatagggaa atcttgttca c tctttatct    780 acttcaaatt gcatgcattt taagaattct ctttgtatgc aaacttcagt a tttatgatt    840 gacataaatc aatattcata tcttcgataa agttaataac tctcctaata c ttatgaata    900 tctcttcctt tacaacccta taaaccccc cactatagct accttcataa t tcatcttag    960 agtaccaacc ctaaatttct tagtgattaa cc atg gct aag aa a agt ctc act    1013
                                    Met Ala Lys Lys Ser Leu Thr
                                     1               5 ttt ctc att tgc att ttc cta ctt ctc aat t ta tgt ttt gca att gag    1061
Phe Leu Ile Cys Ile Phe Leu Leu Leu Asn L eu Cys Phe Ala Ile Glu
         10                 15                    20 aac gta gaa act atg caa aaa tcg gat tca t cg tca caa gat aaa gaa    1109
Asn Val Glu Thr Met Gln Lys Ser Asp Ser S er Ser Gln Asp Lys Glu
     25                  30                    35 tta gat tgg ttt cat ccg tgg ttc cat cca c at cca tgg tgg cta cat    1157
Leu Asp Trp Phe His Pro Trp Phe His Pro H is Pro Trp Trp Leu His
 40                  45                    50                  55 cca cat cca tgg cca ttc gtt cat ccg cca a tg cca gct ggc ggt ttt    1205
Pro His Pro Trp Pro Phe Val His Pro Pro M et Pro Ala Gly Gly Phe
                 60                  65                    70 cat cat gca tgg cca ttc ccc cat cca ccg a tg cct gct ggt ggt ttt    1253
His His Ala Trp Pro Phe Pro His Pro Pro M et Pro Ala Gly Gly Phe
             75                  80                    85 aag ttt cct cat caa taa tttcatcgtc atccatggcc a ttcatgcat          1301
Lys Phe Pro His Gln
             90 ccaccagttc catctccacc taaaggagac aagaattaat tgaaaatatg a agagaagtg    1361 ttggatcaac atcttattga tcacatattt ttctttaggt taatatcttt a ggatttatg    1421 tcttaggtta ttttttgataa aaattaaaat aaatgtacgt tctagggtag t tattataat    1481 ttcttagatt tttccaagta gctttcgatg gtagaaatgt tattaatttg a ttcggctta    1541 tcatgaaata aaatccgtag tattattgct ttagctttta tgatttgtag t tattttatg    1601 ttgattgttc tccattt                                                   1618
```

<210> SEQ ID NO 2
<211> LENGTH: 92
<212> TYPE: PRT
<213> ORGANISM: Nicotiana tabacum

<400> SEQUENCE: 2

```
Met Ala Lys Lys Ser Leu Thr Phe Leu Ile C ys Ile Phe Leu Leu Leu
 1               5                  10                    15

Asn Leu Cys Phe Ala Ile Glu Asn Val Glu T hr Met Gln Lys Ser Asp
             20                  25                    30

Ser Ser Ser Gln Asp Lys Glu Leu Asp Trp P he His Pro Trp Phe His
         35                  40                    45
```

```
Pro His Pro Trp Trp Leu His Pro His Pro T rp Pro Phe Val His Pro
     50                  55                  60

Pro Met Pro Ala Gly Gly Phe His His Ala T rp Pro Phe Pro His Pro
 65                  70                  75                  80

Pro Met Pro Ala Gly Gly Phe Lys Phe Pro H is Gln
                     85                  90

<210> SEQ ID NO 3
<211> LENGTH: 30
<212> TYPE: DNA
<213> ORGANISM: Nicotiana tabacum
<220> FEATURE:
<223> OTHER INFORMATION: desc/NTM19-specific syntheti c oligo-nucleotide-

<400> SEQUENCE: 3
tgcaaaacat aaattgagaa gtaggaaaat                                    30

<210> SEQ ID NO 4
<211> LENGTH: 30
<212> TYPE: DNA
<213> ORGANISM: Brassica napus
<220> FEATURE:
<223> OTHER INFORMATION: /desc = synthetic o ligonucleotide (primer 1)
      used for amplification of the Bp 4A promoter

<400> SEQUENCE: 4
gtcgacaagc ttctaaaaat agcaataact                                    30

<210> SEQ ID NO 5
<211> LENGTH: 30
<212> TYPE: DNA
<213> ORGANISM: Brassica napus
<220> FEATURE:
<223> OTHER INFORMATION: /desc = synthetic o ligonucleotide (primer 2)
      used for the amplification of th e Bp4A promoter

<400> SEQUENCE: 5
ggatcctcta gaaagagatg aagtattcta                                    30
```